United States Patent
Biber et al.

(10) Patent No.: US 8,436,614 B2
(45) Date of Patent: May 7, 2013

(54) LOCAL COIL ARRANGEMENT FOR MAGNETIC RESONANCE APPLICATIONS WITH ACTIVATABLE MARKER

(75) Inventors: Stephan Biber, Erlangen (DE); Peter Heubes, Poxdorf (DE); Wilfried Schnell, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 608 days.

(21) Appl. No.: 12/639,566

(22) Filed: Dec. 16, 2009

(65) Prior Publication Data
US 2010/0156412 A1 Jun. 24, 2010

(30) Foreign Application Priority Data
Dec. 17, 2008 (DE) .......................... 10 2008 063 457

(51) Int. Cl.
*G01R 33/20* (2006.01)
(52) U.S. Cl.
USPC .......................................... 324/318; 324/322
(58) Field of Classification Search .......... 324/300–322; 600/407–435; 382/128–132; 606/1, 32, 606/41
See application file for complete search history.

(56) References Cited

U.S. PATENT DOCUMENTS

| | | | | |
|---|---|---|---|---|
| 6,466,018 B1 * | 10/2002 | Dumoulin et al. | ............ | 324/318 |
| 7,343,194 B2 * | 3/2008 | Ferris et al. | ............ | 600/415 |
| 7,452,357 B2 * | 11/2008 | Vlegele et al. | ............ | 606/32 |
| 7,833,221 B2 * | 11/2010 | Voegele et al. | ............ | 606/41 |
| 2004/0204642 A1 * | 10/2004 | Ferris et al. | ............ | 600/410 |
| 2006/0089624 A1 * | 4/2006 | Voegele et al. | ............ | 606/1 |
| 2006/0089625 A1 * | 4/2006 | Voegele et al. | ............ | 606/1 |
| 2006/0089626 A1 * | 4/2006 | Vlegele et al. | ............ | 606/1 |
| 2009/0118610 A1 * | 5/2009 | Karmarkar et al. | ............ | 600/420 |
| 2009/0253978 A1 * | 10/2009 | Hashimshony et al. | ............ | 600/407 |
| 2010/0156412 A1 * | 6/2010 | Biber et al. | ............ | 324/307 |
| 2011/0043207 A1 * | 2/2011 | Gross et al. | ............ | 324/318 |
| 2011/0210735 A1 * | 9/2011 | Trakic et al. | ............ | 324/309 |

FOREIGN PATENT DOCUMENTS

WO WO 2008/135873 11/2008
WO WO 2009152586 A1 * 12/2009

* cited by examiner

*Primary Examiner* — Melissa Koval
*Assistant Examiner* — Tiffany Fetzner
(74) *Attorney, Agent, or Firm* — Schiff Hardin LLP

(57) ABSTRACT

A local coil arrangement for magnetic resonance applications has a base body in which at least one local coil is arranged. An excitation signal to excite an examination subject to emit a magnetic resonance signal can be emitted by the local coil and/or a magnetic resonance signal emitted by the examination subject can be received by means of said local coil. At least one volume region is present in the base body, in which an amount of a substance is located that can be excited by means of the coil or another coil so as to emit a magnetic resonance signal. A shielding is arranged in the base body. The shielding can be controlled so as to either shield or not shield the volume region depending on the control state, so that the volume region is occluded or visible with regard to magnetic resonance applications.

8 Claims, 3 Drawing Sheets

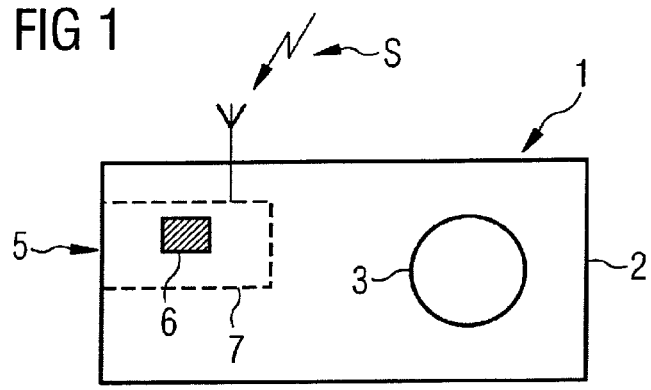
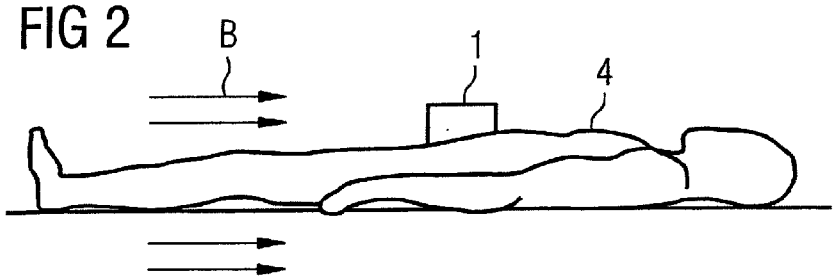
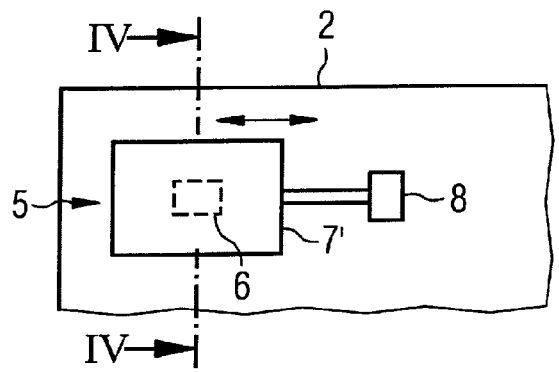
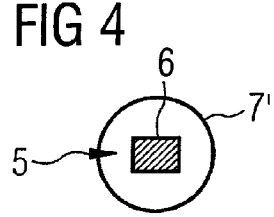

LOCAL COIL ARRANGEMENT FOR MAGNETIC RESONANCE APPLICATIONS WITH ACTIVATABLE MARKER

BACKGROUND OF THE INVENTION

1. Field of the Invention

The present invention concerns a local coil arrangement for magnetic resonance applications, of the type wherein the local coil arrangement has a base body and at least one local coil is arranged in the base body, and wherein an excitation signal to excite an examination subject to emit a magnetic resonance signal is emitted by the local coil and/or a magnetic resonance signal emitted by the examination subject is received, and wherein at least one volume region is present in the base body, in which volume region is located an amount of a substance that can be excited by the coil or another coil to emit a magnetic resonance signal.

2. Description of the Prior Art

Local coil arrangements of the above type are known.

In magnetic resonance examinations, local coil arrangements are normally used that can be freely positioned on the top of the patient ("anterior" if the patient is located in a dorsal position) within defined limits. However, for magnetic resonance examinations it has proven to be advantageous to know not only the approximate but rather the precise position of the local coil arrangement.

In the prior art, before the actual measurement an overview magnetic resonance image is produced from which the position of the local coil arrangement can be calculated automatically with certain precision limits if, for example, "characteristic antenna profiles" of the local coil are known. However, ambiguities (that can be caused by the use of multiple local coil arrangements or the use of one local coil arrangement with multiple local coils, for example) cause difficulties. Therefore, a method that is not based on the characteristic antenna profiles would be preferred.

To solve this problem, it is known to embed items known as "markers" into the base body. The "marker" is a substance that can be localized in a magnetic resonance image. The "marker" is therefore arranged in a volume region. It is composed of an amount of a substance that can be excited by the coil or a different coil to emit a magnetic resonance signal.

If the substance is the same substance that is also detected in the actual examination (for example hydrogen nuclei), the market itself can even be visible in the actual patient examination. This interferes as an aliasing artifact in the phase coding directions.

Alternatively, it is possible to use nuclei of other elements as markers, for example 31P or 19F. In this case, however, the entire radio-frequency system of the magnetic resonance system (transmission system, reception system and antenna system) must be able to transmit and to receive on the corresponding other frequency. Corresponding multiple applications that increase the price of the magnetic resonance system are required for this.

SUMMARY OF THE INVENTION

An object of the present invention is to provide a local coil arrangement that avoids the aforementioned problems.

According to the invention, a local coil arrangement of the aforementioned type is augmented by a shielding arranged in the base body, the shielding being controlled to either shield or not shield the volume region in which the substance is located depending on the control state, so that the volume region is occluded or visible with regard to the magnetic resonance applications.

With this embodiment it is possible use an arbitrary substance—even the substance of the actual usable measurement—as a marker substance. Nevertheless, the actual usable imaging is not disrupted. The detectability of the marker can be switched via corresponding activation of the shielding.

In a first embodiment of the present invention, the shielding is formed by a shield element and a mechanical actuator, and the shield element is mechanically moved to change the control state of the shielding by the mechanical actuator.

For example, the shield element can have a first shield part and a second shield part. In this case, the shield parts can be moved relative to one another by the mechanical actuator to change the control state of the shielding.

Both shield parts can be moved, or the first shield part can be stationary relative to the volume region. To change the control state of the shielding, in this case only the second shield part is mechanically moved by the mechanical actuator.

Alternatively, the shield element can be mechanically moved as a unit relative to the volume region by the mechanical actuator to change the control state of the shielding.

It is also possible for the shielding to be stationary relative to the volume region. In this case, the shielding has a switching device with at least one switching element. The switch state of the switching device is changed to charge the control state of the shielding.

The at least one switching element can in principle be arbitrarily fashioned. An embodiment as a PIN diode or MEMS switch is preferable.

The control signal to set the control state of the shielding and possibly also the energy for the mechanical actuator can in principle be supplied to the shielding in an arbitrary manner, for example via cables, electrically or optically. It is preferable that the control signal of the shielding is supplied without conductors.

BRIEF DESCRIPTION OF THE DRAWINGS

FIG. 1 schematically illustrates a local coil arrangement.

FIG. 2 schematically illustrates the local coil arrangement in an examination subject in a magnetic field.

FIG. 3 schematically illustrates a first embodiment of the shielding.

FIG. 4 is a section through FIG. 3 along line IV-IV.

DESCRIPTION OF THE PREFERRED EMBODIMENTS

Figure 5:
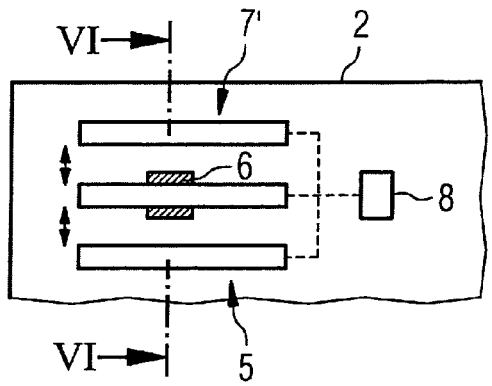
FIG. 5 schematically illustrates a second embodiment of a shielding in accordance with the invention.

According to FIG. 1, a coil arrangement 1 for magnetic resonance applications has a base body 2. The base body 2 is formed of material that is neutral for magnetic resonance applications, for example of a suitable plastic. Such plastics are known.

At least one local coil 3 is arranged in the base body 2. A magnetic resonance signal that is emitted by an examination subject 4—see FIG. 2—is normally receivable by means of the local coil 3. Alternatively, it is possible that an excitation signal that excites nuclei in the examination subject 4 to emit the magnetic resonance signal is emitted by means of the local coil 3. Alternation between these two modes of operation is also conceivable. The examination subject 4 is located in a strong magnetic field B during the emission of the magnetic resonance signal and during the excitation. The magnetic resonance signals of the atomic nuclei of hydrogen are normally excited and detected. However, the excitation of other atomic nuclei is alternatively conceivable, for example of phosphorus-31 or fluorine-19.

Furthermore, a volume region 5 is present in the base body 2, in which an amount of a substance 6 is located that can be excited to emit a magnetic resonance signal. In exceptional cases, the excitation of the substance 6 can ensue by means of the coil 3 that is arranged in the base body 2. However, the excitation of the substance 6 normally ensues by means of a different coil, for example a whole-body coil of a magnetic resonance system. The substance 6 can be arbitrarily selected as long as it can be excited to emit a magnetic resonance signal. In particular, the substance can be water so that the spins of the atomic hydrogen nuclei (thus protons) represent the active substance with regard to the magnetic resonance application.

According to FIG. 1, a shielding 7 is furthermore arranged in the base body 2. The shielding 7 is controllable by a control signal S. Depending on the control state, the shielding 7 either shields the volume region 5 in which the substance 6 is located or does not shield it. For this reason (namely because both states are possible), the shielding 7 in FIG. 1 is indicated with dashed lines.

The shielding 7 is able to shield radio-frequency electromagnetic fields that are required for magnetic resonance imaging. If the shielding 7 shields the volume region 5, the volume region 5 is therefore occluded with regard to the magnetic resonance application. The substance 6 thus does not affect the imaging and also causes no signal disruptions which can lead to artifacts, for example. If the shielding 7 does not shield the volume region 5, the substance 6 is visible in a magnetic resonance image. Therefore it is in particular possible to initially control the shielding 7 such that it does not shield the volume region 5. In this control state of the shielding 7 an overview image is generated, for example by means of a whole-body coil of a magnetic resonance system. The substance 6 (and therefore implicitly the local coil arrangement 1) is localized using the overview image. The shielding 7 is then activated such that it shields the volume region 5. The actual measurement of the examination subject 4 ensues in this control state of the shielding 7.

The control signal S can be supplied to the shielding 7 in an arbitrary manner. A feed in the form of a wired electrical signal, in the form of a wired optical signal or wirelessly (for example as a radio signal, as shown in FIG. 1) is possible.

Switching of the shielding 7 can be accomplished in various ways. According to FIG. 3 through 6, for example, it is possible that the shielding 7 possesses a shield element 7' and a mechanical actuator 8. In this case, the shield element 7' is moved mechanically to change the control state of the shielding 7 by means of the mechanical actuator 8.

According to FIGS. 3 and 4, for example, the shield element 7' can be fashioned as a unit. In this case, the shield element 7' is moved mechanically as a unit relative to the volume region 5 by means of the mechanical actuator 8. The shield element 7' and/or the volume region 5 can hereby be movable relative to the base body 2.

Figure 6:
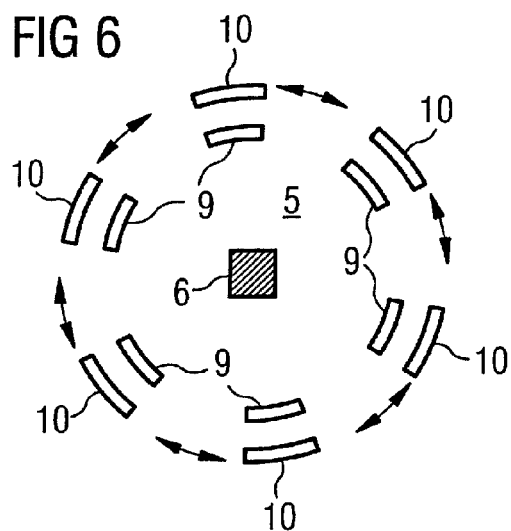
FIG. 6 is a section along a line VI-VI in FIG. 5.

Alternatively, according to FIGS. 5 and 6 the shield element 7' can alternatively possess a first shield part 9 and a second shield part 10. In this case the shield parts 9, 10 are moved relative to one another by means of the mechanical actuator 8 to change the control state of the shielding 7.

In the embodiment of FIGS. 5 and 6, it is possible that both shield parts 9, 10 are moved relative to the volume region 5, in particular are moved in opposite directions relative to one another. However, it is preferable that the first shield part 9 is arranged stationary relative to the volume region 5. In this case, only the second shield part 10 is mechanically moved to change the control state of the shielding 7 by means of the mechanical actuator 8. The shield parts 9, 10 are capacitively or inductively coupled with one another such that they achieve a sufficient shielding effect.

Figure 7:
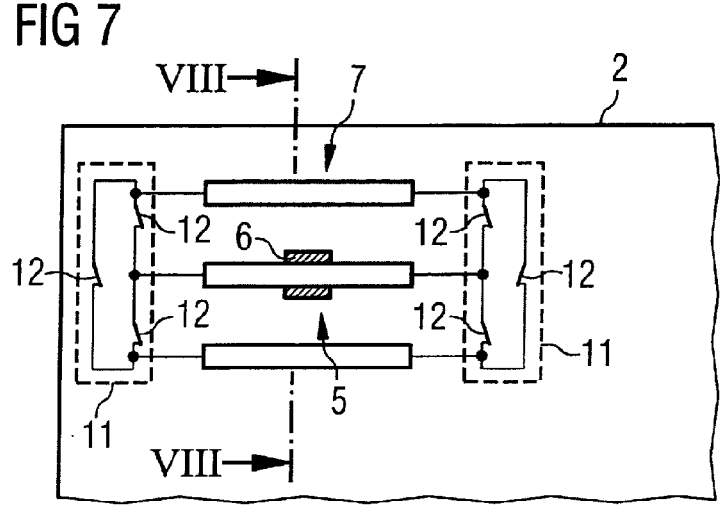
FIG. 7 schematically illustrates a third embodiment of a shielding.
Figure 8:
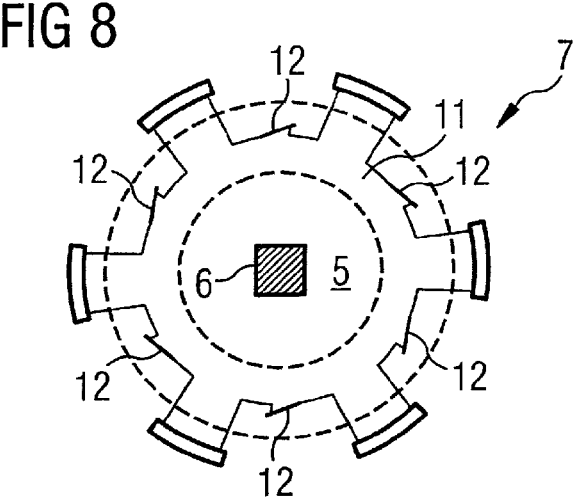
FIG. 8 is a section through FIG. 7 along line VIII-VIII.

As an alternative to FIG. 3 through 6, it is furthermore possible that the shielding 7 is arranged stationary relative to the volume region 5. This embodiment is subsequently explained in detail in connection with FIGS. 7 and 8. In this case, the shielding 7 has a switching device 11 with at least one switching element 12. A switch state of the switching device 11 depends on the control state of the shielding 7 (and vice versa).

Figure 9:
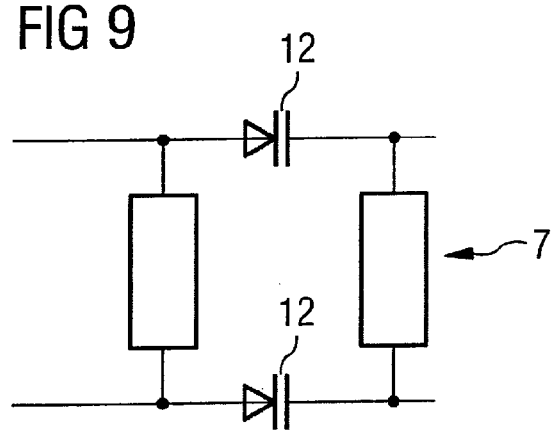
FIG. 9 schematically illustrates a first embodiment of a switching element in accordance with the invention.

The at least one switching element 12 can in principle be arbitrarily fashioned. According to FIG. 9, an embodiment of the at least one switching element 12 as a PIN diode is preferable. In this case a switching of the shielding 7 between its different control states is in particular possible without having to be mechanically moved without parts. This embodiment is therefore particularly reliable in long-term operation.

Figure 10:
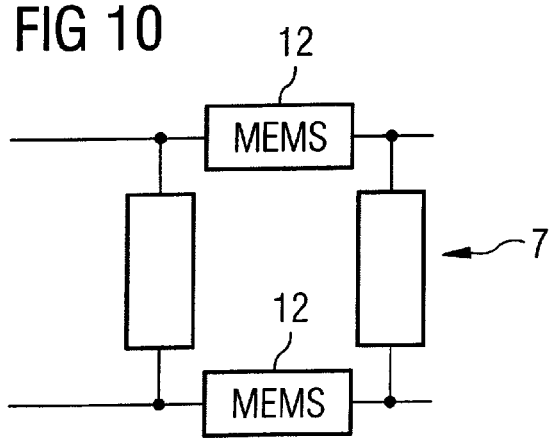
FIG. 10 schematically illustrates a second embodiment of a switching element in accordance with the invention.

Alternatively, according to FIG. 10 it is possible that the at least one switching element 12 is fashioned as a mechanical switch. Here an embodiment as a MEMS switch corresponding to the representation of FIG. 10 is considered.

Since real switches always also exhibit parasitic elements (feed line inductances, capacitances, path resistances etc.) at the operating frequency of the local coil arrangement, possible additional compensation elements ($\lambda/4$ conductors, compensation capacitances/inductances) can be used in order to optimize the complete arrangement at the operating frequency.

The present invention has many advantages. In particular, due to the control capability of the shielding 7 a conflict between the marker functionality of the substance 6 with the signal acquisition in the normal magnetic resonance data acquisition is remedied.

Although modifications and changes may be suggested by those skilled in the art, it is the intention of the inventors to embody within the patent warranted hereon all changes and modifications as reasonably and properly come within the scope of their contribution to the art.

We claim as our invention:

1. A magnetic resonance local coil arrangement comprising:
    a base body;
    a local coil mounted to said base body, said local coil being configured at least to receive magnetic resonance signals emitted due to excitation of nuclei in an examination subject in a volume region in said base body in which a marker substance is located that also emits a magnetic resonance signal upon excitation of nuclei in said marker substance;
    said base body comprising a controllable shielding and a control element that controls said shielding; and said control element being configured to be selectively placed in either of a first control state or a second control state and being configured, in said first control state, to cause said shielding to not shield said volume region containing the marker substance so that magnetic resonance signals emitted from said volume region containing the marker substance contribute to a magnetic resonance image, and being configured, in said second control state, to cause said shielding to shield said volume region containing the marker substance so that magnetic resonance signals emitted from said volume region containing the marker substance do not contribute to a magnetic resonance image.

2. A magnetic resonance local coil arrangement as claimed in claim 1 wherein said shielding comprises:

a movable shield element and wherein said control element is a mechanical actuator, said shield element being mechanically moved by said mechanical actuator, depending on whether said mechanical actuator is in said first control state or said second control state, in order to respectively not shield or in order to respectively shield said volume region containing the marker substance.

3. A magnetic resonance local coil arrangement as claimed in claim 2 wherein said shield element comprises:

a first shield part and a second shield part, said first and second shield parts being movable relative to each other by said mechanical actuator.

4. A magnetic resonance local coil arrangement as claimed in claim 3 wherein said first shield part is stationary relative to said volume region containing the marker substance, and wherein said mechanical actuator moves only said second shield part.

5. A magnetic resonance local coil arrangement as claimed in claim 2 wherein said shield element is a unitary element that is moved as a whole by said mechanical actuator.

6. A magnetic resonance local coil arrangement as claimed in claim 1 wherein said shielding is stationary relative to said volume region, and wherein said control component comprises:

a switching device comprising at least one switching element that is switchable between said first and second controls states.

7. A magnetic resonance local coil arrangement as claimed in claim 6 wherein said at least one switching element is selected from the group consisting of:

PIN diodes and

MEMS switches.

8. A magnetic resonance local coil arrangement as claimed in claim 1 wherein said control element is configured to receive a control signal wirelessly that changes said control element between said first and second control states.

\* \* \* \* \*